(12) United States Patent
Blanco Fernandez et al.

(10) Patent No.: US 7,105,698 B2
(45) Date of Patent: Sep. 12, 2006

(54) PROCESS FOR THE SEPARATION OF R(−)-AND S(+)-5-[2-[[2-(2-ETHOXYPHENOXY)ETHYL]AMINO]PROPYL]-2-METHOXYBENZENESULFONAMIDE

(75) Inventors: Cristina Blanco Fernandez, Boecillo (ES); Antonio Lorente Bonde-Larsen, Boecillo (ES); Jorge Martin Juarez, Boecillo (ES); Luis Octavio Silva Guisasola, Boecillo (ES)

(73) Assignee: Ragactives, S.L., Boecillo (ES)

( * ) Notice: Subject to any disclaimer, the term of this patent is extended or adjusted under 35 U.S.C. 154(b) by 12 days.

(21) Appl. No.: 10/799,909

(22) Filed: Mar. 12, 2004

(65) Prior Publication Data

US 2005/0004398 A1    Jan. 6, 2005

Related U.S. Application Data

(63) Continuation of application No. PCT/ES03/00357, filed on Jul. 11, 2003.

(30) Foreign Application Priority Data

Jul. 12, 2002    (ES) ................. 200201638

(51) Int. Cl.
*C07C 303/42*    (2006.01)
*C07C 303/44*    (2006.01)

(52) U.S. Cl. .................. 564/86; 562/100; 562/401; 562/435

(58) Field of Classification Search .................. 564/86; 562/100, 401, 435
See application file for complete search history.

(56) References Cited

U.S. PATENT DOCUMENTS

| 5,447,958 A | 9/1995 | Niigata et al. | |
| 2003/0109752 A1* | 6/2003 | Hoorn et al. | .................. 564/86 |

FOREIGN PATENT DOCUMENTS

| CZ | 290 708 | * | 1/2002 |
| ES | 2 000 382 | | 2/1988 |
| ES | 2 029 838 | | 10/1992 |
| WO | WO 03/037856 A1 | | 5/2003 |

* cited by examiner

*Primary Examiner*—Peter O'Sullivan
(74) *Attorney, Agent, or Firm*—Akin Gump Strauss Hauer & Feld, LLP (57) ABSTRACT

The process for separating the R(−)- and S(+)-5-[2-[[2-(2-ethoxyphenoxy)ethyl]amino]propyl]-2-methoxybenzenesulfonamide enantiomers comprises (a) reacting a mixture of said enantiomers with an optically active organic acid to form diastereoisomeric salts with said enantiomers, where in said diastereoisomeric salts have different solubility and can be separated by crystallization; (b) separating the diastereoisomeric salt mixture enriched in the salt of one of the enantiomers; and (c) releasing said salts to obtain the R(−)or S(+) enantiomer. The R(−)-5-[2-[[2-(2-ethoxyphenoxy)ethyl]amino]propyl]-2-methoxybenzenesulfonamide enantiomer has α-adrenergic blocking activity and is useful as an antihypertensive agent suitable for the treatment of congestive heart failure and benign prostatic hypertrophy.

22 Claims, 3 Drawing Sheets

PROCESS FOR THE SEPARATION OF R(-)-AND S(+)-5-[2-[[2-(2-ETHOXYPHENOXY)ETHYL]AMINO]PROPYL]-2-METHOXYBENZENESULFONAMIDE

CROSS-REFERENCE TO RELATED APPLICATIONS

This application is a continuation of International Application No. PCT/ES03/000357, filed Jul. 11, 2003, and the disclosure of which is incorporated herein by reference.

BACKGROUND OF THE INVENTION

The invention is related to obtaining the R(-)- and S(+)-5-[2-[[2-(2-ethoxyphenoxy)ethyl]amino]propyl]-2-methoxybenzenesulfonamide enantiomers, with a high degree of optical purity, by means of the separation of the diastereoisomeric salts which are formed from a mixture containing said enantiomers with an optically active acid, as well as to the development of a method which allows determining the degree of optical purity of said enantiomers once they are separated.

European patent EP 34432 discloses sulfamoyl-substituted phenethylamine derivatives exhibiting α-adrenergic blocking activity, useful as antihypertensive agents suitable for the treatment of congestive heart failure. Among said compounds is 5-[2-[[2-(2-ethoxyphenoxy)ethyl]amino]propyl]-2-methoxybenzenesulfonamide (I), one of the enantiomers of which, specifically the R(-)-enantiomer, known as Tamsulosin, is useful in the treatment of congestive heart failure and benign prostatic hypertrophy.

Prior studies have proven that the pharmacological action of the R(-)-5-[2-[[2-(2-ethoxyphenoxy)ethyl]amino]propyl]-2-methoxybenzenesulfonamide enantiomer, hereinafter R(-)-I, is up to 320 times greater than that of its S(+)-5-[2-[[2-(2-ethoxyphenoxy)ethyl]amino]propyl]-2-methoxybenenesulfonnamide enantiomer, hereinafter S(+)-I [Honda, K., Nakagawa, Ch., Terai, M., *Naunyn-Schimiedeberg's Arch. Pharmacol.* (1987), 336(3): 295–302; Honda, K., Nakagawa, Ch., Momose, N., *J. Pharm. Pharmacol.* (1987), 39(4): 316–18]. Therefore, it is necessary to obtain the optically pure R(-)-I enantiomer substantially free of the S(+)-I enantiomer. It is also necessary to have an industrial process for the production of the R(-)-I enantiomer.

European patent EP 34432 discloses a process for the preparation of said compound of formula (I) although it does not disclose the obtainment of its optical isomers.

U.S. Pat. No. 4,731,478 discloses in its examples a process for obtaining the R(-)-I and S(+)-I enantiomers from the condensation of R(-)- or S(+)-5-[(2-amino-2-methyl)ethyl]-2-methoxybenzenesulfonamide with 2-(o-ethoxyphenoxy)ethyl bromide.

European patents EP 257787 and EP 380144 disclose a process for obtaining the R(-)-I enantiomer from the synthesis of the R(-)-5-((2-amino-2-methyl)ethyl)-2-methoxybenzene-sulfonamide chiral amine, in its optically pure form, and later condensation reaction by reductive amination or by nucleophilic substitution.

Until now, however, no reference has been found in the literature regarding methods for the resolution of compound (I).

BRIEF SUMMARY OF THE INVENTION

The invention confronts the problem of providing an alternative process for obtaining the R(-)-I enantiomer, with high optical purity, useful for use as a drug, susceptible to being applied at an industrial level.

The solution provided by this invention is based on the fact that the inventors have observed that some optically active organic acids are capable of forming, with the R(-)-I and S(+)-I enantiomers, diastereoisomeric salts of different solubility in the reaction medium, which allows their separation by crystallization. By letting the mixture of said diastereoisomeric salts crystallize in the reaction medium or in a suitable solvent, because of their different solubility, the crystals formed will be enriched in one of the diastereoisomeric salts and, accordingly, in one of the enantiomers, preferably in the R(-)-I enantiomer. The separation of the diastereoisomeric salts and their subsequent release yields the R(-)-I enantiomer with a high degree of optical purity, susceptible to being used as a drug.

The invention also provides a solution to the problem of quantitatively determining the optical purity of said R(-)-I, S(+)-I enantiomers or of their mixtures, which is based on derivatizing said enantiomers with (-)-menthyl chloroformate and analyzing the corresponding diastereoisomeric carbamates obtained by means of high performance liquid chromatography (HPLC).

Therefore, in one aspect, the invention is related to a process for separating the R(-)-I enantiomer or the S(+)-I enantiomer from a mixture containing said enantiomers, comprising (i) placing said enantiomer mixture in contact, in a solvent, with an optically active organic acid to form diastereoisomeric salts with said enantiomers, wherein said diastereoisomeric salts have different solubility in said solvent and can be separated by crystallization, (ii) separating the diastereoisomeric salt mixture enriched in the diastereoisomeric salt of one of the enantiomers, and (iii) releasing the previously separated diastereoisomeric salt mixture to obtain the R(-)-I or S(+)-I enantiomer or a mixture enriched in one of them.

The process provided by this invention allows obtaining the R(-)-I enantiomer with an optical purity equal to or greater than 99% by means of successive recrystallizations or resuspensions of the mixtures of the diastereoisomeric salts to gradually enrich said mixtures in the diastereoisomeric salt of the R(-)-I enantiomer. The R(-)-I compound thus obtained can be used as an active ingredient in pharmaceutical preparations.

In another aspect, the invention is related to a diastereoisomeric salt formed by the R(-)-I enantiomer or the S(+)-I enantiomer and an enantiomer of an optically active organic acid.

In another aspect, the invention is related to a method for determining the degree of optical purity of the R(-)-I, S(+)-I enantiomers or of their mixtures, which comprises derivatizing said enantiomers with (-)-menthyl chloroformate and analyzing the diastereoisomeric carbamate derivatives obtained by means of HPLC. Said diastereoisomeric carbamate derivatives, as well as their obtainment process, constitute additional aspects of this invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

In a first aspect, the invention is related to a process for separating the R(−)-I enantiomer or the S(+)-I enantiomer from a mixture containing said R(−)-I and S(+)-I enantiomers, comprising:

(a) placing a mixture containing the R(−)-I and S(+)-I enantiomers in contact, in a solvent, with an optically active organic acid to form diastereoisomeric salts with said R(−)-I and S(+)-I enantiomers, wherein said diastereoisomeric salts have different solubility in said solvent and can be separated by crystallization;

(b) separating the diastereoisomeric salt mixture enriched in the R(−)-I or S(+)-I enantiomer diastereoisomeric salt formed in step (a); and (c) releasing the diastereoisomeric salt mixture separated in (b) to obtain the R(−)-I or S(+)-I enantiomer or a mixture enriched in one of them.

This process can be completely or partially repeated, a variable number of times, to obtain the desired enantiomer with greater optical purity. In this sense, the enriched diastereoisomeric salt mixture can be resuspended or recrystallized again, once or several times, in a solvent, which can be the same one used in the reaction or another suitable solvent, until reaching the desired degree of optical purity in the separated enantiomer.

The enantiomer mixture can contain said R(−)-I and S(+)-I enantiomers at any relative proportion to one another. In a particular embodiment, said enantiomer mixture is a racemic mixture. The compound of general formula (I), in its racemic form, can be obtained by means of any of the methods disclosed in the literature, for example, by means of the process disclosed in U.S. Pat. No. 4,373,106, comprising the reductive amination of 4-methoxy-3-sulfonamidephenylacetone with 2-(2-ethoxyphenoxy)ethylamine.

Figure 1:
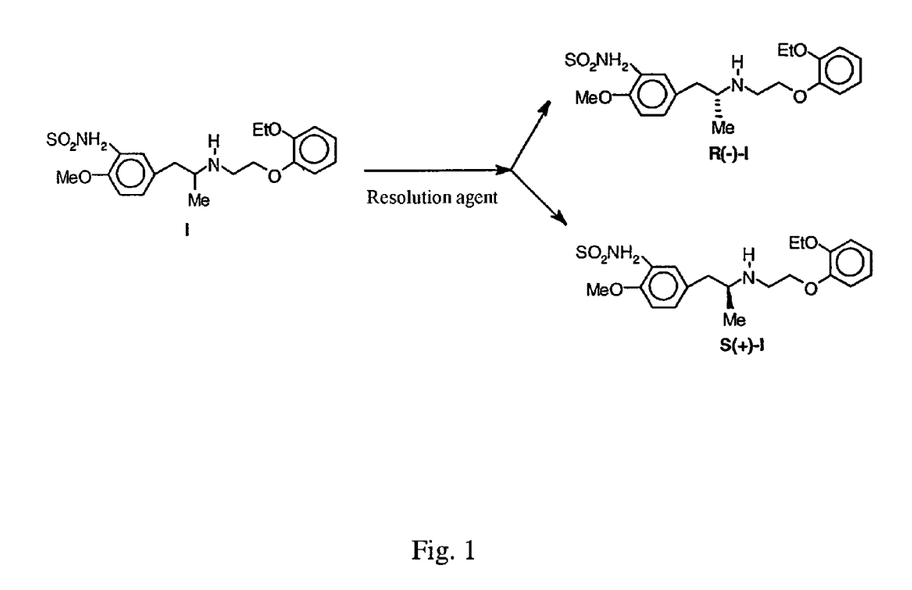
FIG. 1 is a reaction equation for separating R(−)-I and S(+)-I enantiomers from a mixture according to one embodiment of the invention.

The process for separating the R(−)-I and S(+)-I enantiomers from a mixture containing them, by means of optical resolution, is shown in FIG. 1.

The process for separating the R(−)-I and S(+)-I enantiomers provided by this invention begins by dissolving or suspending the mixture containing the R(−)-I and S(+)-I enantiomers in a suitable solvent. Examples of suitable solvents include water, alcohols, ketones, nitriles or mixtures thereof. In a particular embodiment, said solvent is a mixture of acetone and water.

A resolution agent is added to said solution or suspension, as shown in FIG. 1. The resolution agent used when putting into practice the process provided by this invention is an optically active organic acid capable of forming diastereoisomeric salts with said R(−)-I and S(+)-I enantiomers, which have different solubility in a given solvent and can be separated by crystallization. For putting into practice the process provided by this invention, it is essential that the diastereoisomeric salts formed comply with the aforementioned conditions.

In a particular embodiment, said optically active organic acid is selected from the group formed by D-10-camphorsulfonic acid, L-10-camphorsulfonic acid, (−)-N-(3,5-dinitrobenzoyl)-α-phenylglycine acid and (+)-N-(3,5-dinitrobenzoyl)-α-phenylglycine acid. The preferred optically active organic acid is D-10-camphorsulfonic acid or L-10-camphorsulfonic acid.

The optically active organic acids forming diastereoisomeric salts with the R(−)-I and S(+)-I enantiomers, wherein said diastereoisomeric salts cannot be separated by crystallization (for example because they form an oil rather than crystals), such as (−)-di-p-toluyl tartaric acid, are not useful for putting into practice the process provided by the present invention [see Example 4].

The amount of optically active organic acid to be added can be from approximately 0.5 to approximately 1.5 equivalents, preferably from approximately 0.7 to 1.1 equivalents, based on the amount of R(−)-I or S(+)-I enantiomer contained in the enantiomer mixture.

For the formation of the diastereoisomeric salts between the optically active organic acid and the R(−)-I and S(+)-I enantiomers, in solution, temperatures are needed which are comprised between room temperature (generally between 15° C. and 20° C. approximately) and the reflux temperature of the solvent used. The diastereoisomeric salts formed can be separated due to their different solubility in the solvent present in the reaction medium, either by means of crystallization or resuspension. To selectively crystallize one of the diastereoisomeric salts, the temperature of the reaction medium can gradually be lowered until reaching the temperature at which the selective crystallization of one of the diastereoisomeric salts over the other salt is achieved. Alternatively, selective crystallization can be achieved by means of stirring the diastereoisomeric salt mixture for a suitable time period. Generally, the first crystals will be enriched in one of the diastereoisomeric salts, although they will contain a certain, lesser amount of the other diastereoisomeric salt. By means of successive recrystallizations or resuspensions, the diastereoisomeric salt mixture can become enriched in one of the R(−)-I or S(+)-I enantiomers up to an enantiomeric excess of 99.5%.

In a particular embodiment, the resuspension of the diastereoisomeric salts is carried out only for a suitable time period and only at a suitable temperature, without needing to recrystallize the diastereoisomeric salts by prior dissolution in the solvent used.

The separation of the diastereoisomeric salt mixture enriched in the R(−)-I or S(+)-I enantiomer can be carried out, based on their different solubility, by any conventional solid/liquid separation method, for example, by filtration. The effective separation of the diastereoisomeric salt mixture enriched in the R(−)-I or S(+)-I enantiomer in the desired degree of optical purity may require one or more recrystallizations or resuspensions of the diastereoisomeric salt mixture.

Once the diastereoisomeric salt mixture enriched in one of the R(−)-I or S(+)-I enantiomers has been separated, the corresponding product enriched in the R(−)-I enantiomer or in the S(+)-I enantiomer is released. This release can be carried out by conventional methods, for example, by means of reaction with a base, such as sodium bicarbonate, sodium hydroxide, sodium carbonate, etc.

Figure 2:
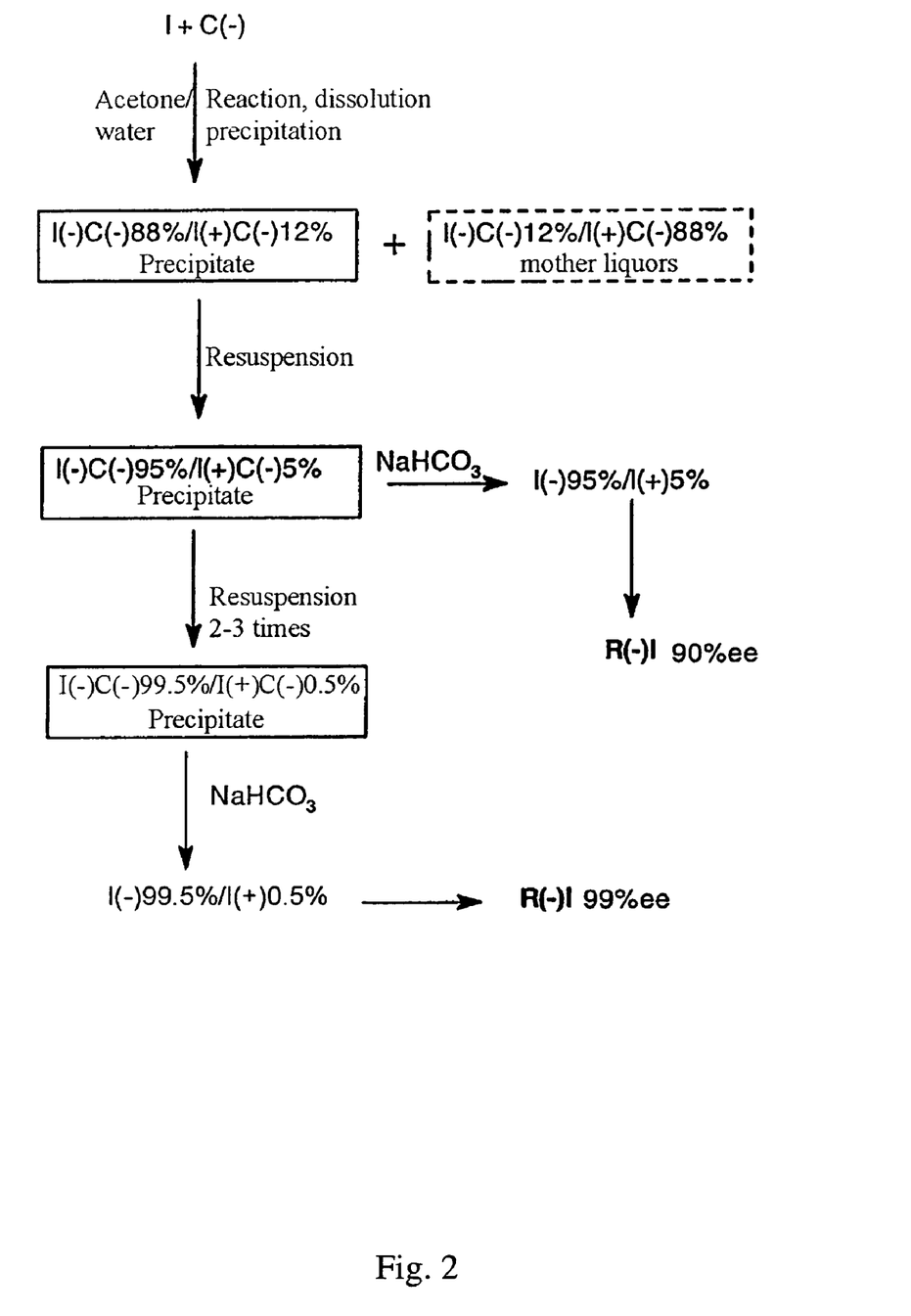
FIG. 2 is a diagram of a process for separating enantiomers from a mixture according to an embodiment of Example 1 of the invention.

In a particular embodiment [see Example 1], the R(−)-I enantiomer is separated by placing an R(−)-I and S(+)-I enantiomer mixture in contact with L-10-camphorsulfonic acid, as shown in FIG. 2. The mixture of R(−)-I and S(+)-I enantiomers reacts with L-10-camphorsulfonic acid [C(−)], in a solvent (acetone/water), to form the I(+)C(−) and I(−)C(−) diastereoisomeric salts. The I(−)C(−) salt precipitates preferably over the I(+)C(−) salt, which mainly remains in the mother liquors. The precipitate obtained, mainly containing the R(−)-I enantiomer with an enantiomeric excess (ee) of up to 88%, can be resuspended in a solvent, which can be the same solvent or another suitable solvent, and is kept at a temperature comprised between room temperature and the reflux temperature, for a time period comprised between 20 and 24 hours, to give rise to a second precipitate. This new precipitate can optionally be neutralized to give rise mainly to the R(−)-I compound with an enantiomeric excess of up to 90%, or it can be resuspended again, once or several more times, in a solvent, which can be the same solvent used previously or another suitable solvent, until achieving the required optical purity, of an enantiomeric excess of up to 99%. The S(+)-I enantiomer can be similarly separated, but using D-10-camphorsulfonic acid in this case.

In another particular embodiment, the R(−)-I enantiomer is separated by reacting a racemic mixture of R(−)-I and S(+)-I with (−)-N-(3,5-dinitrobenzoyl)-α-phenylglycine acid in acetonitrile/water [see Example 3].

The process for separating the R(−)-I and S(+)-I enantiomers provided by this invention can also be carried out, if so desired, by means of the alternating and separate use of two different optically active organic acids capable of forming diastereoisomeric salts with said R(−)-I and S(+)-I enantiomers, wherein said salts have different solubility in a given solvent and can be separated by crystallization. Said particular embodiment comprises:

(a) placing an R(−)-I and S(+)-I enantiomer mixture in contact, in a solvent, with a first optically active organic acid to form diastereoisomeric salts with said R(−)-I and S(+)-I enantiomers, wherein said diastereoisomeric salts have different solubility in said solvent and can be separated by crystallization, under conditions allowing the formation of a first precipitate;

(b) separating said first precipitate from the mother liquors, said mother liquors mainly containing one of said diastereoisomeric salts formed in step (a), either the R(−)-I enantiomer or the S(+)-I enantiomer, and isolating the diastereoisomeric salt mixture enriched in the R(−)-I or S(+)-I enantiomer contained in said mother liquors;

(c) releasing the R(−)-I and S(+)-I enantiomers present in the diastereoisomeric salt mixture enriched in the R(−)-I or S(+)-I enantiomer, isolated from the mother liquors in step (b), by cleavage of said diastereoisomeric salts, generating a medium comprising a mixture of the R(−)-I or S(+)-I enantiomers enriched in one of said enantiomers, and said first optically active organic acid;

(d) removing said first optically active organic acid from the reaction medium;

(e) placing said enantiomer mixture enriched in R(−)-I or S(+)-I obtained in step (c), substantially free of said first optically active organic acid, in contact, in a solvent, with a second optically active organic acid, different from the optically active organic acid used in step (a), to form the corresponding diastereoisomeric salts of said R(−)-I or S(+)-I enantiomers with said second optically active acid, wherein said diastereoisomeric salts have different solubility in said solvent and can be separated by crystallization, under conditions allowing the formation of a second precipitate and where the salt corresponding to the majority R(−)-I or S(+)-I enantiomer preferably precipitates in the reaction medium;

(f) separating said second precipitate formed in step (e) from the mother liquors, said second precipitate containing a mixture of the diastereoisomeric salts formed in step (e) enriched in the diastereoisomeric salt corresponding to the majority R(−)-I or S(+)-I enantiomer, and (g) releasing the precipitated diastereoisomeric salts, enriched in the R(−)-I or S(+)-I enantiomer, to obtain the enantiomer mixture enriched in the R(−)-I or S(+)-I enantiomer.

The two different optically active organic acids used in steps (a) and (e) are chosen such that the one used in step (a) forms a diastereoisomeric salt with one of the R(−)-I or S(+)-I enantiomers, for example, with the S(+)-I enantiomer, which is less soluble then that of the other enantiomer, such that mainly the diastereoisomeric salt of said enantiomer precipitates, and the optically active organic acid used in step (e) is chosen such that it forms a diastereoisomeric salt with the other one of the enantiomers, R(−)-I or S(+)-I, in this case with the less soluble R(−)-I enantiomer, such that mainly the diastereoisomeric salt of said second enantiomer precipitates. The person skilled in the art will understand that, in accordance with the invention, multiple combinations can be made with the objective of separating the desired enantiomer.

The optically active organic acids which can be used in steps (a) and (e) can be any of those acids forming diastereoisomeric salts complying with the different, previously mentioned solubility and separation by crystallization conditions. In a particular embodiment, the optically active organic acids used in steps (a) and (e) are the different enantiomers of an optically active organic acid, for example the D- and L- enantiomers of 10-camphorsulfonic acid, or the (+) or (−) enantiomers of N-(3,5-dinitrobenzoyl)-α-phenylglycine acid. In another particular embodiment, the optically active organic acids used in steps (a) and (e) are particular enantiomers of different optically active organic acids, for example, D-10-camphorsulfonic acid can be used in step (a) and (−)-N-(3,5-dinitrobenzoyl)-α-phenylglycine acid can be used in step (e).

By means of the cleavage of the diastereoisomeric salts [step (c)] by conventional methods, on one hand, a mixture enriched in the R(−)-I and S(+)-I enantiomers and, on the other hand, said first optically active organic acid used in step (a), which must be removed from the reaction medium so that it does not interfere in step (e) in the formation of diastereoisomeric salts with the second optically active organic acid, are released into the reaction medium. The removal of said first optically active organic acid can be carried out by conventional methods, for example by extraction and separation of phases, depending on the nature thereof.

If so desired, to obtain a greater optical purity, said second precipitate separated in step (f) can be resuspended, in a solvent, which can be the same solvent as the one used in step (e) or another, different solvent, once or several times, to give rise to a new precipitate comprising a diastereoisomeric salt mixture even more enriched in one of the R(−)-I or S(+)-I enantiomers, for its later release.

Figure 3:
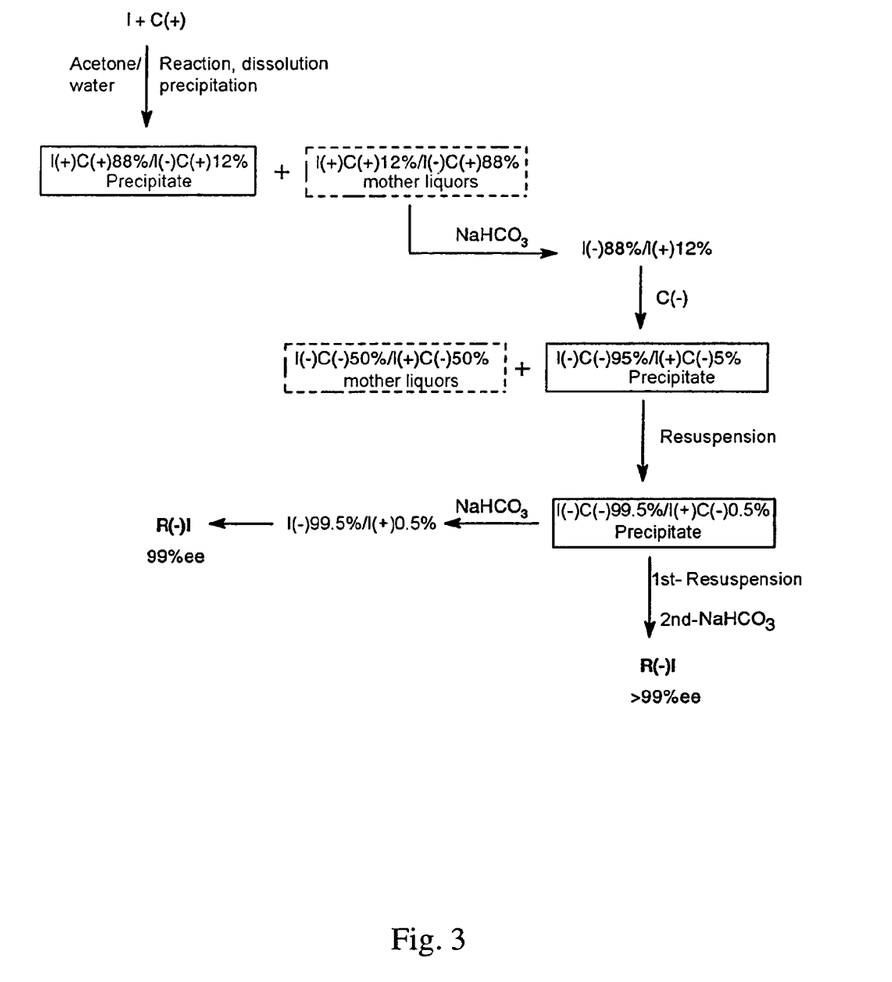
FIG. 3 is a diagram of a process for separting enantiomers from a mixture according to an embodiment of Example 2 of the invention.

In a particular embodiment [see Example 2], briefly represented in FIG. 3, said first optically active organic acid is D-10-camphorsulfonic acid [C(+)] and the second one is L-10-camphorsulfonic acid [C(−)]. The D-10-camphorsulfonic acid [C(+)] is reacted in an acetone/water mixture (solvent) with a racemic mixture of R(−)-I and S(+)-I, to form the I(+)C(+) and I(−)C(+) diastereoisomeric salts, the I(+)C(+) salt precipitating preferably over the I(−)C(+) salt. The resulting mother liquors, enriched in the I(−)C(+) salt, are concentrated to dryness and the residue obtained is dissolved in a non-miscible solvent/water mixture, it is neutralized with a suitable base, such as sodium bicarbonate, to yield an enantiomer mixture mainly containing the R(−)-I enantiomer [I(−) in FIG. 3]. The second optically active organic acid [C(−)] is added to the resulting product to form the I(−)C(−) and I(+)C(−) diastereoisomeric salts, the I(−)C(−) salt precipitating preferably over the I(+)C(−) salt. This second precipitate thus obtained can be neutralized again with a suitable base, such as sodium bicarbonate, to yield an enantiomer mixture mainly containing the R(−)-I enantiomer with an enantiomeric excess of 90%, or, alternatively, said second precipitate can be resuspended in a solvent (which can be the same solvent previously used or another suitable solvent) at a temperature comprised between room temperature and the reflux temperature of the solvent, for a time period comprised between 20 and 24 hours, to give rise to a new precipitate, which is either neutralized to mainly yield the R(−)-I enantiomer with a high degree of optical purity, for example with an enantiomeric excess of approximately 99%, or said new precipitate is resuspended again, one time or more, until obtaining the R(−)-I enantiomer with the desired purity. The R(−)-I enantiomer with a very high optical purity (an enantiomeric excess of 99%) can be obtained by operating in this manner.

The S(+)-I enantiomer can be similarly obtained. To do so, L-10-camphorsulfonic acid is firstly added to the enantiomer mixture and, after isolating and neutralizing the mother liquors, D-10-camphorsulfonic acid is added.

In another aspect, the invention is related to a diastereoisomeric salt formed by the R(−)-I enantiomer or S(+)-I enantiomer and an optically active organic acid, wherein said optically active acid is capable of forming diastereoisomeric salts with said R(−)- and S(+)-I enantiomers with different solubility in a given solvent, and said diastereoisomeric salts can be separated by crystallization. In a particular embodiment, said diastereoisomeric salt is selected from:

the diastereoisomeric salt of the R(−)-5-[2-[[2-(2-ethoxyphenoxy)ethyl]amino]propyl]-2-methoxybenzenesulfonamide enantiomer and D-10-camphorsulfonic acid;

the diastereoisomeric salt of the R(−)-5-[2-[[2-(2-ethoxyphenoxy)ethyl]amino]propyl]-2-methoxybenzenesulfonamide enantiomer and L-10-camphorsulfonic acid;

the diastereoisomeric salt of the S(+)-5-[2-[[2-(2-ethoxyphenoxy)ethyl]amino]propyl]-2-methoxybenzenesulfonamide enantiomer and D-10-camphorsulfonic acid;

the diastereoisomeric salt of the S(+)-5-[2-[[2-(2-ethoxyphenoxy)ethyl]amino]propyl]-2-methoxybenzenesulfonamide enantiomer and L-10-camphorsulfonic acid;

the diastereoisomeric salt of the R(−)-5-[2-[[2-(2-ethoxyphenoxy)ethyl]amino]propyl]-2-methoxybenzenesulfonamide enantiomer and (−)-N-(3,5-dinitrobenzoyl)-α-phenylglycine;

the diastereoisomeric salt of the R(−)-5-[2-[[2-(2-ethoxyphenoxy)ethyl]amino]propyl]-2-methoxybenzenesulfonamide enantiomer and (+)-N-(3,5-dinitrobenzoyl)-α-phenylglycine;

the diastereoisomeric salt of the S(+)-5-[2-[[2-(2-ethoxyphenoxy)ethyl]amino]propyl]-2-methoxybenzenesulfonamide enantiomer and (−)-N-(3,5-dinitrobenzoyl)-α-phenylglycine; and the diastereoisomeric salt of the S(+)-5-[2-[[2-(2-ethoxyphenoxy)ethyl]amino]propyl]-2-methoxybenzenesulfonamide enantiomer and (+)-N-(3,5-dinitrobenzoyl)-α-phenylglycine.

On the other hand, as is well known, the rotatory power described for the R(−)-I and S(+)-I enantiomers, in their hydrochloric form, is (−) or (+) 4, at a concentration of c=0.35, using methanol as a solvent [Merck Index, Edition XII, item number 9217]. This rotatory power value is too low to allow quantitatively establishing the optical purity of each one of the enantiomers in a reliable manner.

For this reason, a method has been developed which allows differentiating the R(−)-I or S(+)-I enantiomers by means of their derivatization using (−)-menthyl chloroformate to form the corresponding diastereoisomeric carbamates, which are susceptible to being analyzed by conventional analytical techniques, for example, by BPLC.

Therefore, in another aspect, the invention is related to a method for determining the degree of optical purity of a composition comprising the R(−)-I enantiomer or the S(+)-I enantiomer, or mixtures of both enantiomers, comprising:

reacting a sample of said composition to be analyzed with (−)-menthyl chloroformate to obtain the corresponding diastereoisomeric carbamate derivatives, and analyzing the diastereoisomeric carbamate derivates obtained in step a) by means of HPLC.

The reaction between the R(−)-I and/or S(+)-I enantiomers with (−)-menthyl chloroformate is carried out in a solvent, in the presence of a base, to obtain the corresponding diastereoisomeric carbamate derivatives. In a particular embodiment, the reaction between said R(−)-I and/or S(+)-I enantiomers with (−)-menthyl chloroformate is carried out in a halogenated solvent, for example dichloromethane, in the presence of diisopropylethylamine, at room temperature, to form the corresponding diastereoisomeric carbamate derivatives.

The diastereoisomeric carbamates obtained are isolated and analyzed by HPLC. In a particular embodiment, said derivatives are analyzed using a Novapack® C-18 column and an acetonitrile/water mixture as an eluent. The diastereoisomeric carbamate derivatives of the R(−)-I and/or S(+)-I enantiomers formed appear as 2 peaks at 210 nm in the chromatograph and their area ratio allows determining the proportion of each one of the enantiomers in the composition to be analyzed. In this manner, and according to the present invention, the optical purity of compositions comprising the R(−)-I and/or S(+)-I enantiomers can be determined.

In another aspect, the invention refers to the two carbamate derivatives, diastereoisomeric to one another, represented by formulas II and III:

Said diastereoisomeric carbamate derivatives of formulas II and III correspond to the compounds obtained when reacting each one of the R(−)-I or S(+)-I enantiomers with (−)-menthyl chloroformate to give the compounds of formulas II or III respectively.

In another aspect, the invention is related to a process for obtaining diastereoisomeric carbamate derivatives which comprises reacting the R(−)-I enantiomer or the S(+)-I enantiomer with (−)-menthyl chloroformate, in a solvent, in the presence of a base. The solvent and the base can be any suitable solvent and base. In a particular embodiment, said solvent is a halogenated solvent, such as dichloromethane, and said base is an amine, such as diisopropylamine. The reaction can be carried out in a wide interval of temperatures, preferably at room temperature.

The following examples serve to illustrate the present invention and should not be considered as limiting thereof.

EXAMPLE 1

Separation of the R(−)-5-[2-[[2-(2-ethoxyphenoxy)ethyl]amino]propyl]-2-Methoxybenzenesulfonamide Enantiomer [R(−)I] by Means of the Use of L-10-Camphorsulfonic Acid 36.7 g of a racemic mixture containing the R(−)-I and S(+)-I enantiomers are resuspended with stirring in 200 ml of an acetone/water mixture (80/20). Then, 23 g (1.1 equivalents) of L-10-camphorsulfonic acid are added, and it is stirred until dissolution.

The solution is seeded with the (−)L-10-camphorsulfonic-R(−)-I salt [I(−)C(−)], by means of which the solution begins to become cloudy, it is maintained with stirring at room temperature for 20–24 hours and is filtered.

The solid obtained is resuspended again in 5 volumes of acetone/water (80/20), first under reflux and then at room temperature, for 20–24 hours, and is filtered again.

The product obtained is dried to give 20.1 g of the I(−)C(−) salt, with a 35% yield.

Example 1.1

Analysis of the R(−)-I Enantiomer Optical Purity

To analyze the obtained R(−)-I enantiomer optical purity, proceed as indicated below:

1 ml of solution saturated with NaHCO$_3$ in water and 1 ml of dichloromethane are added to a sample of approximately 70 mg of the product obtained in Example 1, it is stirred for 5 minutes and the phases are separated. Then, 0.5 ml of the organic phase are transferred to a test tube and 1 ml of a 0.1 M solution of diisopropylethylamine in anhydrous dichloromethane and 1 ml of a 0.1 M solution of (−)-menthyl chloroformate in the same solvent are added. The mixture is stirred for several minutes and 1 ml of water is added. The reaction can be checked by thin layer chromatography (TLC) using tetrahydrofurane (THF)/heptane/methanol (25/25/1) as an eluent. 0.4 ml of the organic phase are extracted and the solvent is vacuum removed. 5 ml of mobile phase are added, and this is analyzed by HPLC using acetonitrile (ACN)/water (65/35) as an eluent, with a flow rate of 1.0 ml/minute; detection at λ=210 nm; and with a Novapack® C-18, 3.9×150 nm column.

The solid obtained, after having been thus analyzed, shows an R(−)-I/S(+)-I enantiomer ratio of 95/5, which indicates an enantiomeric excess of 90% for R(−)-I.

The precipitated and dried salt is resuspended with stirring in 780 ml of ethyl acetate and 300 ml of 7% NaHCO$_3$ solution, and is heated to 40–45° C. until obtaining a solution. The phases are separated and the organic phase is washed again two times with 200 ml of water, and then a concentrated hydrochloric acid solution is added, adjusting the pH between 5 and 5.5. Then, the solvent is partially distilled at reduced pressure, to half the volume, and it is left to cool, the product precipitating as R(−)-I.HCl. Once dried, the collected product weighs 12 g (0.025 moles), obtaining an overall yield equal to 30%.

EXAMPLE 2

Separation of the R(−)-5-[2-[[2-(2-ethoxyphenoxy)ethyl]amino]propyl]-2-Methoxybenzenesulfonamide Enantiomer [R(−)I] by Means of the Use of D and L-10-Camphorsulfonic Acids 46.89 g of a racemic mixture of R(−)-I and S(+)-I resuspended in 705 ml of acetone with 5% water are heated to 40–45° C., and 18.6 g (0.7 equivalents) of D-10-camphorsulfonic acid are incorporated. Once it is all dissolved under heat, it is left to cool at room temperature, seeding with the (+) salt of D-10-camphorsulfonic-S(+)-I [I(+)C(+)] acid. The suspension obtained is left to stir at room temperature for 20–24 hours and is filtered. The residue obtained from the mother liquors is resuspended in 705 ml of dichloromethane and 705 ml of 7% NaHCO$_3$, and is stirred until dissolution.

After separating the phases, the organic phase is taken to residue and is replaced by 235 ml of acetone containing 20% water, to which 29.33 g (1.1 equivalents) of L-10-camphorsulfonic acid are added, stirring until dissolution.

It is seeded with the L-10-camphorsulfonic-R(−)-I (−) salt [I(−)C(−)], by means of which the solution begins to become cloudy, it is maintained with stirring at room temperature for 20–24 hours and is filtered. The solid obtained is resuspended in 5 volumes of acetone containing 20% water, it is taken to reflux for 30 minutes, it is left stirring at 20–25° C.

for 20 hours, is filtered and dried to give 17.65 g (0.027 moles, 24% yield) of a white solid.

The optical purity of the R(−)-I enantiomer contained in the I(−)C(−) salt is analyzed using the process described in Example 1.1. The solid obtained shows a 99.5/0.5 ratio of the R(−)-I/S(+)-I enantiomers, which indicates a 99% enantiomeric excess for R(−)-I.

The precipitated and dried salt is resuspended with stirring in 680 ml of ethyl acetate and 255 ml of 7% NaHCO$_3$ solution, and is heated to 40–45° C., until obtaining a solution. The phases are separated and the organic phase is washed again two times with 170 ml of water, and then, a concentrated hydrochloric acid solution is added, adjusting the pH between 5 and 5.5. The solvent is partially distilled under reduced pressure, to half the volume, and is left to cool, the product precipitating as R(−)-I.HCl. Once dried, the collected product weighs 11.5 g (0.025 moles), an overall yield of 22% being obtained.

EXAMPLE 3

Separation of the R(−)-5-[2-[[2-(2-ethoxyphenoxy)ethyl]amino]propyl]-2-methoxybenzenesulfonamide Enantiomer [R(−)I] by Means of the Use of(−)-N-(3,5-dinitrobenzoyl)-α-phenylglycine Acid 10 g of a racemic mixture of the R(−)-I and S(+)-I enantiomers resuspended in 300 ml of acetonitrile with 20% water are heated until dissolution, and 4.2 g (0.5 equivalents) of (−)-N-(3,5-dinitrobenzoyl)-α-phenylglycine acid are incorporated. The solution formed is slowly cooled to room temperature and is left stirring for 20–25 hours.

The solid formed is isolated and is subjected to analysis, using (−)-menthyl chloroformate, using the method described in Example 1.1, giving rise to an R(−)-I/S(+)-I mixture (86/14). The yield obtained is 5.8 g of the salt formed.

EXAMPLE 4

Separation of Racemic Mixture of 5-[2-[[2-(2-ethoxyphenoxy)ethyl]amino]propyl]-2-Methoxybenzenesulfonamide with (−)-di-p-toluyl Tartaric Acid 10 g of a racemic mixture of the R(−)-I and S(+)-I enantiomers resuspended in 50 ml of a 5% mixture of n-propanol are heated until dissolution, and 9.46 g (1 equivalent) of (−)-di-p-toluyl tartaric acid are incorporated. The solution formed is slowly cooled to room temperature and is left stirring for 20–25 hours.

Well formed crystals precipitate, which are isolated by filtration. The salt obtained is neutralized in an ethyl acetate and sodium hydroxide mixture to isolate the resulting base.

The rotatory power of the product obtained is measured at a concentration of c=0.35 in methanol, obtaining a value of practically 0, which indicates that neither of the two [R(−)-I] or [S(+)-I] enantiomers has been selectively isolated.

Later recrystallizations or the use of other solvents: methanol, acetone, acetonitrile, ethyl acetate, butanol or isopropanol, or their mixtures with water, resulted in the precipitation of the diastereoisomeric salts, such as a gum, or such as a precipitate in which the diastereoisomeric salts obtained are at 50% [once released, the base has rotatory power of zero or practically zero].

It will be appreciated by those skilled in the art that changes could be made to the embodiments described above without departing from the broad inventive concept thereof.

It is understood, therefore, that this invention is not limited to the particular embodiments disclosed, but it is intended to cover modifications within the spirit and scope of the present invention as defined by the appended claims.

We claim:

1. A process for separating the R(−)-5-[2-[[2-(2-ethoxyphenoxy)ethyl]amino]propyl]-2-methoxybenzenesulfonamide enantiomer [R(−)-I]or S(+)-[2-[[2-(2-ethoxyphenoxy)ethyl]amino]propyl]-2-methoxybenzenesulfonamide enantiomer [S(+)-I] from a mixture of said R(−)-I and S(+)-I enantiomers, comprising:
   (a) placing a mixture containing the R(−)-I and S(+)-I enantiomers in contact, in a solvent, with an optically active organic acid selected from the group consisting of (−)-N-(3,5-dinitrobenzoyl)-α-phenyl-glycine, (+)-N-(3,5-dinitrobenzoyl)-α-phenyl-glycine, and non-racemic mixtures thereof, to form diastereoisomeric salts with said R(−)-I and S(+)-I enantiomers, wherein said diastereoisomeric salts have different solubility in said solvent and can be separated by crystallization;
   (b) separating the diastereoisomeric salt mixture enriched in the diastereoisomeric salt of the R(−)-I or S(+)-I enantiomer formed in step (a); and
   (c) releasing the diastereoisomeric salt mixture separated in step (b) to obtain the R(−)-I or S(+)-I enantiomer or a mixture enriched in one of them.

2. Process according to claim 1, wherein prior to carrying out step (c), the diastereoisomeric salt mixture enriched in the diastereoisomeric salt of the R(−)-I or S(+)-I enantiomer separated in step (b) is resuspended or recrystallized, one time or more.

3. Process according to claim 1, wherein said mixture containing the R(−)-I and S(+)-I enantiomers is a racemic mixture.

4. A process for separating the R(−)-5-[2-[[2-(2-ethoxyphenoxy)ethyl]amino]propyl]-2-methoxybenzenesulfonamide enantiomer [R(−)-I] or S(+)-[2-[[2-(2-ethoxyphenoxy)ethyl]amino]propyl]-2-methoxybenzenesulfonamide enantiomer [S(+)-I] from a mixture of said R(−)-I and S(+)-I enantiomers, comprising.
   (a) placing a mixture containing the R(−)-I and S(+)-I enantiomers in contact, in a solvent, with an optically active organic acid to form diastereoisomeric salts with said R(−)-I and S(+)-I enantiomers, wherein said diastereoisomeric salts have different solubility in said solvent and can be separated by crystallization;
   (b) separating the diastereoisomeric salt mixture enriched in the diastereoisomeric salt of the R(−)-I or S(+)-I enantiomer formed in step (a); and
   (c) releasing the diastereoisomeric salt mixture separated in step (b) to obtain the R(−)-I or S(+)-I enantiomer or a mixture enriched in one of them,
   further comprising the alternating and separate use of two different optically active organic acids, capable of forming diastereoisomeric salts with said R(−)-I and S(+)-I enantiomers, wherein said salts have different solubility in a given solvent and can be separated by crystallization.

5. Process according to claim 4 wherein said solvent is selected from the group formed by water, alcohols, ketones, nitriles and their mixtures.

6. Process according to claim 5, wherein said solvent is a mixture of acetone and water.

7. Process according to claim 1, wherein said diastereoisomeric salts are formed at a temperature comprised between 15° C. and the reflux temperature of the solvent.

8. Process according to claim 1, wherein the separation of the diastereoisomeric salt mixture enriched in the R(−)-I or S(+)-I enantiomer is carried out by crystallization and separation of the crystals formed.

9. Process according to claim 1, wherein the separation of the diastereoisomeric salt mixture enriched in the R(−)-I or S(+)-I enantiomer comprises carrying out one or more recrystallizations or resuspensions of said diastereoisomeric salt mixture.

10. Process according to claim 1, wherein the release of the diastereoisomeric salt mixture enriched in one of the R(−)-I or S(+)-I enantiomers separated in step (b) is carried out by means of reaction with a base.

11. Process according to claim 1, wherein the separated enantiomer is the R(−)-I enantiomer.

12. Process according to claim 1, wherein the optically active organic acid used comprises (−)-N-(3,5-dinitrobenzoyl)-α-phenylglycine acid.

13. Process according to claim 1 for the separation of the R(−)-I enantiomer, comprising:
placing a mixture of R(−)-I and S(+)-I enantiomers in contact with (−)-N-(3,5-dinitrobenzoyl)-α-phenyl-glycine [C(−)], to form the I(+)C(−) and I(−)C(−) diastereoisomeric salts, in a solvent in which mainly the I(−)C(−) salt precipitates over the I(+)C(−) salt;
separating the precipitate comprising mainly I(−)C(−) diastereoisomeric salt over the I(+)C(−) salt and resuspending it in a solvent;
maintaining the resulting suspension at a temperature comprised between 15° C. and the reflux temperature of the solvent, for a time period comprised between 20 and 24 hours, to obtain a second precipitate mainly comprising the I(−)C(−) salt;
and if so desired,
neutralizing said second precipitate to mainly obtain the R(−)-I enantiomer, or
resuspending said second precipitate, one time or more, in a solvent, to obtain the R(−)-I enantiomer with the desired optical purity.

14. A diastereoisomeric salt selected from:
the diastereoisomeric salt of the R(−)-5-[2-[[2-(2-ethoxyphenoxy)ethyl]amino]propyl]-2-methoxybenzenesulfonamide enantiomer and (−)-N-(3,5-dinitrobenzoyl)-α-phenylglycine;
the diastereoisomeric salt of the R(−)-5-[2-[[2-(2-ethoxyphenoxy)ethyl]amino]propyl]-2-methoxybenzenesulfonamide enantiomer and (+)-N-(3,5-dinitrobenzoyl)-α-phenylglycine;
the diastereoisomeric salt of the S(+)-5-[2-[[2-(2-ethoxyphenoxy)ethyl]amino]propyl]-2-methoxybenzenesulfonamide enantiomer and (−)-N-(3,5-dinitrobenzoyl)-α-phenylglycine; and
the diastereolsomeric salt of the S(+)-5-[2-[[2-(2-ethoxyphenoxy)ethyl]amino]propyl]-2-methoxybenzenesulfonamide enantiomer and (+)-N-(3,5-dinitrobenzoyl)-α-phenylglycine.

15. Process according to claim 4, comprising:
(a) placing an R(−)-I and S(+)-I enantiomer mixture in contact, in a solvent, with a first optically active organic acid to form diastereoisomeric salts with said enantiomers, wherein said diastereoisomeric salts have different solubility in said solvent and can be separated by crystallization, under conditions allowing the formation of a first precipitate;
(b) separating said first precipitate from the mother liquors, said mother liquors mainly containing one of said diastereoisomeric salts formed in step (a), and isolating the diastercoisomeric salt mixture enriched in the R(−)-I or S(+)-I enantiomer contained in said mother liquors;
(c) releasing the R(−)-I and S(+)-I enantiomers present in the diastereoisomeric salt mixture enriched in the R(−)-I or S(+)-I enantiomer, isolated from the mother liquors in step (b), by cleavage of said diastereoisomeric salts, generating a medium comprising a mixture of the R(−)-I or S(+)-I enantiomers enriched in one of said enantiomers, and said first optically active organic acid;
(d) removing said first optically active organic acid from the reaction medium;
(e) placing said enantiomer mixture enriched in R(−)-I or S(+)-I obtained in step (c), substantially free of said first optically active organic acid removed in step d), in contact, in a solvent, with a second optically active organic acid, different from the optically active organic acid used in step (a), to form the corresponding diastereoisomeric salts of said R(−)-I or S(+)-I enantiomers with said second optically active acid, wherein said diastereoisomeric salts have different solubility in said solvent and can be separated by crystallization, under conditions allowing the formation of a second precipitate and where the salt corresponding to the majority R(−)-I or S(+)-I enantiomer preferably precipitates in the reaction medium;
(f) separating said second precipitate formed in step (e) from the mother liquors, said second precipitate containing a mixture of the diastereoisomeric salts formed in step (e) enriched in the diastereoisomeric salt corresponding to the majority R(−)-I or S(+)-I enantiomer; and
(g) releasing the precipitated diastereoisomeric salts, enriched in the R(−)-I or S(+)-I enantiomer, to obtain the enantiomer mixture enriched in the R(−)-I or S(+)-I enantiomer.

16. Process according to claim 15, wherein said optically active organic acids used in steps (a) and (e) are the enantiomers of an optically active organic acid.

17. Process according to claim 16, wherein said optically active organic acids used in steps (a) and (e) are the D- and L-enantiomers of 10-camphorsulfonic acid, or the (+) or (−) enantiomers of N-(3,5-dinitrobenzoyl)-α-phenylglycine acid.

18. Process according to claim 15, wherein said second precipitate separated in step (f) is resuspended in a solvent, one time or more, to give rise to a new precipitate comprising a diastereoisomeric salt mixture enriched in one of the R(−)-I or S(+)-I enantiomers.

19. Process according to claim 15 for the separation of the R(−)-I enantiomer, wherein the first optically active acid is D-10-camphorsulfonic acid and the second optically active acid is L-10-camphorsulfonic acid [C(−)].

20. Process according to claim 15 for the separation of the R(−)-I enantiomer, comprising:
placing an R(−)-I and S(+)-I enantiomer mixture in contact with D-10-camphorsulfonic acid [C(+)], to form the I(+)C(+) and I(−)C(+) diastereoisomeric salts, in a solvent in which mainly the I(+)C(+) salt precipitates over the I(−)C(+) salt;
separating the mother liquors enriched in I(−)C(+) diastereoisomeric salt, isolating the salts contained therein and neutralizing them with a base to obtain an enantiomer mixture mainly containing the R(−)-I enantiomer, and removing the C(+) released after the neutralization of the mother liquors;

putting the enantiomer mixture enriched in R(−)-I in contact with the L-10-camphorsulfonic acid [C(−)], to form the I(−)C(−) and I(+)C(−) diastereoisomeric salts, in a solvent in which the I(−)C(−) salt mainly precipitates over the I(+)C(−) salt; and if so desired, neutralizing the precipitate obtained in the previous step with a base to obtain an enantiomer mixture mainly containing the R(−)-I enantiomer; or resuspending said precipitate in a solvent and maintaining the suspension at a temperature comprised between room temperature and the reflux temperature, for a time period comprised between 20 and 24 hours, generating a new precipitate; and if so desired, neutralizing said new precipitate to mainly obtain the R(−)-I enantiomer; or resuspending said new precipitate, one time or more, until obtaining the R(−)-I enantiomer with the desired optical purity.

21. Process according to claim 1, wherein said solvent comprises acetonitrile and water.

22. A process for separating the R(−)-5-[2-[[2-(2-ethoxyphenoxy)ethyl]amino]propyl]-2-methoxybenzenesulfonamide enantiomer [R(−)-I] or S(+)-[2-[[2-(2-ethoxyphenoxy)ethyl]amino]propyl]-2-methoxybenzenesulfonamide enantiomer [S(+)-I] from a mixture of said R(−)-I and S(+)-I enantiomers, comprising combining two different optically active organic acids capable of forming diastereoisomeric salts with said R(−)-I and S(+)-I enantiomers, in an alternating and separate manner with said enantiomers, wherein said salts have different solubility in a given solvent and can be separated by crystallization.

* * * * *